US006265837B1

(12) United States Patent
Akiyama et al.

(10) Patent No.: US 6,265,837 B1
(45) Date of Patent: Jul. 24, 2001

(54) CHARGED-PARTICLE BEAM IRRADIATION METHOD AND SYSTEM

(75) Inventors: Hiroshi Akiyama, Hitachi; Kazuo Hiramoto, Hitachiota; Koji Matsuda, Hitachi, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/265,557

(22) Filed: Mar. 9, 1999

(30) Foreign Application Priority Data

Mar. 10, 1998 (JP) .................................................. 10-057695

(51) Int. Cl.$^7$ .................................................... H05H 13/04
(52) U.S. Cl. ........................ 315/503; 315/501; 313/359.1; 250/505.1; 250/492.3
(58) Field of Search .................................... 315/503, 501; 313/359.1; 250/505.1, 492.3

(56) References Cited

U.S. PATENT DOCUMENTS

| 5,363,008 | 11/1994 | Hiramoto et al. ...................... 313/62 |
| 5,969,367 | * 10/1999 | Hiramoto et al. .................. 250/492.3 |

FOREIGN PATENT DOCUMENTS

A-9-223600    8/1997 (JP) .

OTHER PUBLICATIONS

Review of Scientific Instruments vol. 64, No. 8 Aug. 1993 American Institute of Physics.
The Darmstadt Program HITAG: heavy ion therapy at GSI, P224 1994 Hadrontherapy in Oncology.
Accelerator Aspects of the Cancer Therapy Project at the GSI Darmstad pp. 2641–2643.

Magnetic scanning system for heavy ion therapy pp. 296–305 Nuclear Instruments and Methods in Physics Research A330 (1993).

Medical Physics, Jul./Aug. 1980 vol. 7, No. 4 pp. 365–369.

Medical Physics, Jan. 1995, vol. 22, No. 1, pp. 37–53.

Medical Physics, May/Jun. 1983 vol. 10, No. 3, pp. 344–346.

* cited by examiner

Primary Examiner—Jack Berman
Assistant Examiner—Nikita Wells
(74) Attorney, Agent, or Firm—Antonelli, Terry, Stout & Kraus, LLP

(57) ABSTRACT

A charged-particle beam irradiation method and system are disclosed in which while a charged-particle beam ejected from an accelerator is scanned by an electromagnet, each layer resulting from the division of an affected part into a plurality of layers in the direction of progression of the charged-particle beam is irradiated with the charged-particle beam. The intensity of a charged-particle beam for irradiation of a first layer is made lower than the intensity of a charged-particle beam for irradiation of a second layer existing at a position deeper than the first layer in the beam progressing direction. A scanning speed in the first layer is changed between a portion of the first layer subjected to irradiation at the time of irradiation of the second layer and a portion of the first layer subjected to no irradiation at the time of irradiation of the second layer.

14 Claims, 11 Drawing Sheets

CHARGED-PARTICLE BEAM IRRADIATION METHOD AND SYSTEM

BACKGROUND OF THE INVENTION

The present invention relates to a charged-particle beam irradiation method and system for performing a medical treatment such as a cancer treatment through irradiation with a charged-particle beam, and more particularly to a charged-particle beam irradiation method and system in which an affected part can be irradiated with a charged-particle beam in conformity of the shape of the affected part.

In the case where a cancer treatment is performed by use of a charged-particle beam such as a proton beam with a high energy generated by an accelerator or the like, it is required that an area having a diameter of about 20 cm should be irradiated with a proton beam having an energy of about 230 MeV at the highest. The conventional method for realizing this has been disclosed by W. T. Chu et al, "Instrumentation for treatment of cancer using proton and light-ion beams", Review of Science Instrument, Vol. 64, No. 8 (August 1993), pp. 2055–2122. In the disclosed method, an affected part is divided into a plurality of layers in the direction of depth in a body and is scanned layer by layer through irradiation with a charged-particle beam in conformity to the shape of each layer.

FIG. 9 shows the construction of a charged-particle beam irradiation system disclosed by the Chu et al's article. Referring to FIG. 9, a charged-particle beam 90 ejected from an accelerator is adjusted in energy by a degrader 17 so that the irradiation of a plurality of layers 210 to 212 in an affected part 202 of a body 201 with the adjusted beam is made in a sequence from a deeper layer to a shallower layer. The beam is scanned by use of first and second scanning electromagnets 31a and 31b which are disposed in the irradiation system so that the directions of deflection are orthogonal or vertical and horizontal in the plane of each layer.

The Chu et al's article has disclosed charged-particle scanning methods including a wobbler scanning method in which a beam is circle-wise scanned, a raster scanning method in which a beam is zigzag-wise scanned, and a pixel scanning method in which a beam is pixel-wise scanned. FIG. 10 shows a charged-particle beam irradiation method based on the raster scanning method. As shown in FIG. 10, a charged-particle beam 220 is zigzag-wise scanned in the first layer 210 in conformity to the shape of the first layer 210. A similar scanning is made in the n-th layer 212.

FIG. 11 shows a dose profile 230 (or a relationship between depth and dose) in the case where the irradiation is made with a charged-particle beam having a high energy and a dose profile 231 in the case where the irradiation is made with a charged-particle beam having a high energy. As shown in FIG. 11, the dose profile of the charged-particle beam has the value 240 or 241 of a dose peak called Bragg peak. A beam penetration depth providing the Bragg peak becomes larger as the energy is higher. It is also shown in FIG. 11 that the irradiation with the charged-particle beam is made with a small dose even at depth portions shallower than the Bragg peak providing portion. Referring to FIG. 10, this shows that when the irradiation with the charged-particle beam 220 is made for the first layer 210, a region 222 of the n-th layer 212 is also subjected to the irradiation with the same charged-particle beam 220. Accordingly, in the case where the irradiation with a charged-particle beam 221 is made for the n-th layer 212, it is required that the dose of a beam portion (indicated by dotted line) for irradiation of the region 222 should be reduced. Though only the first layer and the n-th layer are shown in FIG. 10 for simplification of illustration, the actual irradiation of the n-th layer amounts to the superimposed irradiation for the first to (n−1)th layers. Therefore, when the irradiation is to be made for the n-th layer, it is necessary that a dose for the beam portion indicated by dotted line in the n-th layer should be equal to or smaller than, for example, one tenth (at the largest ratio) as compared with a dose for a beam portion indicated by solid line.

For such requirements, the Chu et al's article has proposed two irradiation methods as follows. In a first method, the scanning speed of a charged-particle beam at the time of irradiation of each layer is constant while the intensity of the charged-particle beam is reduced when the region 222 is irradiated. In a second method, the intensity of a charged-particle beam at the time of irradiation of each layer is constant while the scanning speed of the charged-particle beam is increased when the region 222 is irradiated. With each of the first and second methods, it is possible to reduce the radiation dose of the charged-particle beam in the region 222.

In the first method, however, it is required that while one layer is being irradiated with a beam, the intensity of the beam should be changed greatly in accordance with an irradiation position. Namely, there is a problem that a large change in intensity of each charged-particle beam, for example, from 1 to ¹/₁₀ is needed in the period of 0.1 to 2 seconds when one layer is irradiated, which complicates the control of the accelerator ejecting the beam.

In the second method, it is required that the scanning speed of a beam at the time of irradiation of the region 222 should be increased to, for example, 10 times, which needs a large change in magnetic field intensity of the scanning electromagnet with time. Accordingly, there is a problem that a power supply voltage of the scanning electromagnet becomes high, thereby increasing the cost of a power supply for the scanning electromagnet.

SUMMARY OF THE INVENTION

An object of the present invention is to provide a charged-particle beam irradiation method and system in which the control of an accelerator ejecting a charged-particle beam is simplified and the cost of a power supply for a scanning electromagnet can be reduced.

A first invention for attaining the above object is characterized in that in a charged-particle beam irradiation method in which while a charged-particle beam ejected from an accelerator is scanned by an electromagnet, each layer resulting from the division of an affected part into a plurality of layers in the direction of progression of the charged-particle beam is irradiated with the charged-particle beam, wherein the intensity of a charged-particle beam for irradiation of a first layer is made lower than the intensity of a charged-particle beam for irradiation of a second layer existing at a position deeper than the first layer in the beam progressing direction, and a scanning speed in the first layer is changed between a portion of the first layer subjected to irradiation at the time of irradiation of the second layer and a portion of the first layer subjected to no irradiation at the time of irradiation of the second layer.

With the construction of the first invention in which the intensity of the charged-particle beam for irradiation of the first layer is made lower than the intensity of the charged-particle beam for irradiation of the second layer, the scanning speed of the charged-particle beam for irradiation of the first layer can be lowered, thereby making it possible to lower a voltage to be applied to the electromagnet. As a result, it is possible to reduce the cost of a power supply for the electromagnet. Also, with the construction in which the scanning speed is changed between the portion of the first layer subjected to irradiation and the portion of the first layer subjected to no irradiation, it is possible to adjust the accumulative dose amount of a portion subjected to superimposed irradiation. Further, since there is no need to make a large change of the intensity of the charged-particle beam in a short time, the control of the accelerator is simplified.

A second invention for attaining the above object is characterized in that in a charged-particle beam irradiation method in which while a charged-particle beam ejected from an accelerator is scanned by an electromagnet, each layer resulting from the division of an affected part into a plurality of layers in the direction of progression of the charged-particle beam is irradiated with the charged-particle beam, wherein the intensity of a charged-particle beam for irradiation of each layer is made lower as the position of that layer becomes shallower in the beam progressing direction, and a scanning speed in a shallower layer is changed between a portion of the shallower layer subjected to irradiation at the time of irradiation of a deeper layer and a portion of the shallower layer subjected to no irradiation at the time of irradiation of the deeper layer.

With the construction in the second invention in which the intensity of the charged-particle beam for irradiation of each layer is made lower as the position of that layer becomes shallower in the beam progressing direction, it is possible to lower a voltage to be applied to the electromagnet. As a result, it is possible to reduce the cost of a power supply for the electromagnet. Also, with the construction in which the scanning speed is changed between the portion of the shallower layer subjected to irradiation and the portion of the shallower layer subjected to no irradiation, it is possible to adjust the accumulative dose amount of a portion subjected to superimposed irradiation is possible. Further, since there is no need to make a large change of the intensity of the charged-particle beam in a short time, the control of the accelerator is simplified.

A third invention for attaining the above object has the features of the first or second invention and is further characterized in that the accelerator includes a synchrotron for ejecting a charged-particle beam through the application of a high-frequency electric field thereto, and the intensity of the charged-particle beam is controlled by controlling the high-frequency electric field.

With the construction in the third invention in which the intensity of the charged-particle beam is controlled by controlling the high-frequency electric field, it is possible to shorten a time required for the change of the beam intensity, thereby shortening a treatment time.

A fourth invention for attaining the above object has the features of the third invention and is further characterized in that the high-frequency electric field is generated from an electrode applied with a high-frequency electric power, and the high-frequency electric field is controlled by controlling the power value of the high-frequency electric power.

With the construction in the fourth invention in which the high-frequency electric field is controlled by controlling the power value of the high-frequency electric power, the control of the high-frequency electric field is simplified.

A fifth invention for attaining the above object has the features of the first or second invention and is further characterized in that the intensity of the charged-particle beam is controlled by controlling the amount of ions injected into the accelerator.

With the fifth invention, since the amount of ions injected into the accelerator can be suppressed to the minimum required, it is possible to reduce unnecessary beams in the accelerator, thereby reducing the (radio) activation of the equipment.

A sixth invention for attaining the above object has the features of the first or second invention and is further characterized in that the scanning of the charged-particle beam is performed on the basis of the dose value of the charged-particle beam.

With the construction in the sixth invention in which the charged-particle beam is scanned on the basis of the dose value thereof, it is possible to control a dose in each layer accurately even if the intensity of the charged-particle beam ejected from the accelerator has some variations.

A seventh invention for attaining the above object has the features of the first or second invention and is further characterized in that a layer to be irradiated with the charged-particle beam is changed by changing the energy of the charged-particle beam, and the change in energy is made by a degrader disposed on an orbit of the charged-particle beam.

With the construction in the seventh invention in which the energy of the charged-particle beam is changed by the degrader, the control of the accelerator is simplified.

An eighth invention for attaining the above object is characterized in that in a charged-particle beam irradiation system in which while a charged-particle beam ejected from an accelerator is scanned by electromagnet means, each layer resulting from the division of an affected part into a plurality of layers in the direction of progression of the charged-particle beam is irradiated with the charged-particle beam, the system comprises intensity control means for making the intensity of a charged-particle beam for irradiation of a first layer lower than the intensity of a charged-particle beam for irradiation of a second layer existing at a position deeper than the first layer in the beam progressing direction, and scanning speed changing means for changing a scanning speed in the first layer between a portion of the first layer subjected to irradiation at the time of irradiation of the second layer and a portion of the first layer subjected to no irradiation at the time of irradiation of the second layer.

With the eighth invention, there are obtained effects similar to those in the first invention.

A ninth invention for attaining the above object is characterized in that in a charged-particle beam irradiation system in which while a charged-particle beam ejected from an accelerator is scanned by electromagnet means, each layer resulting from the division of an affected part into a plurality of layers in the direction of progression of the charged-particle beam is irradiated with the charged-particle beam, the system comprises intensity control means for making the intensity of the charged-particle beam for irradiation of each layer lower as the position of that layer becomes shallower in the beam progressing direction, and scanning speed changing means for changing a scanning speed in a shallower layer between a portion of the shallower layer subjected to irradiation at the time of irradiation of a deeper layer and a portion of the shallower layer subjected to no irradiation at the time of irradiation of the deeper layer.

With the ninth invention, there are obtained effects similar to those in the second invention.

A tenth invention for attaining the above object has the features of the eighth or ninth invention and is further characterized in that the intensity control means is constructed to control the intensity of the charged-particle beam by controlling a high-frequency electric field applied when the charged-particle beam is ejected from the accelerator.

With the tenth invention, there are obtained effects similar to those in the third invention.

An eleventh invention for attaining the above object has the features of the tenth invention and is further characterized in that the intensity control means is constructed to control the high-frequency electric field by controlling the power value of a high-frequency electric power applied to an electrode which generates the high-frequency electric field when the charged-particle beam is ejected from the accelerator.

With the eleventh invention, there are obtained effects similar to those in the fourth invention.

A twelfth invention for attaining the above object has the features of the eighth or ninth invention and is further characterized in that the intensity control means is constructed to control the intensity of the charged-particle beam by controlling the amount of ions injected into the accelerator.

With the twelfth invention, there are obtained effects similar to those in the fifth invention.

A thirteenth invention for attaining the above object has the features of the eighth or ninth invention and is further characterized in that there is provided electromagnet control means for controlling the electromagnet on the basis of the dose value of the charged-particle beam.

With the thirteenth invention, there are obtained effects similar to those in the sixth invention.

A fourteenth invention for attaining the above object has the features of the eighth or ninth invention and is further characterized in that there is provided a degrader disposed on an orbit of the charged-particle beam for making the change in energy of the charged-particle beam.

With the fourteenth invention, there are obtained effects similar to those in the seventh invention.

DESCRIPTION OF THE PREFERRED EMBODIMENTS (Embodiment 1)

Figure 1:
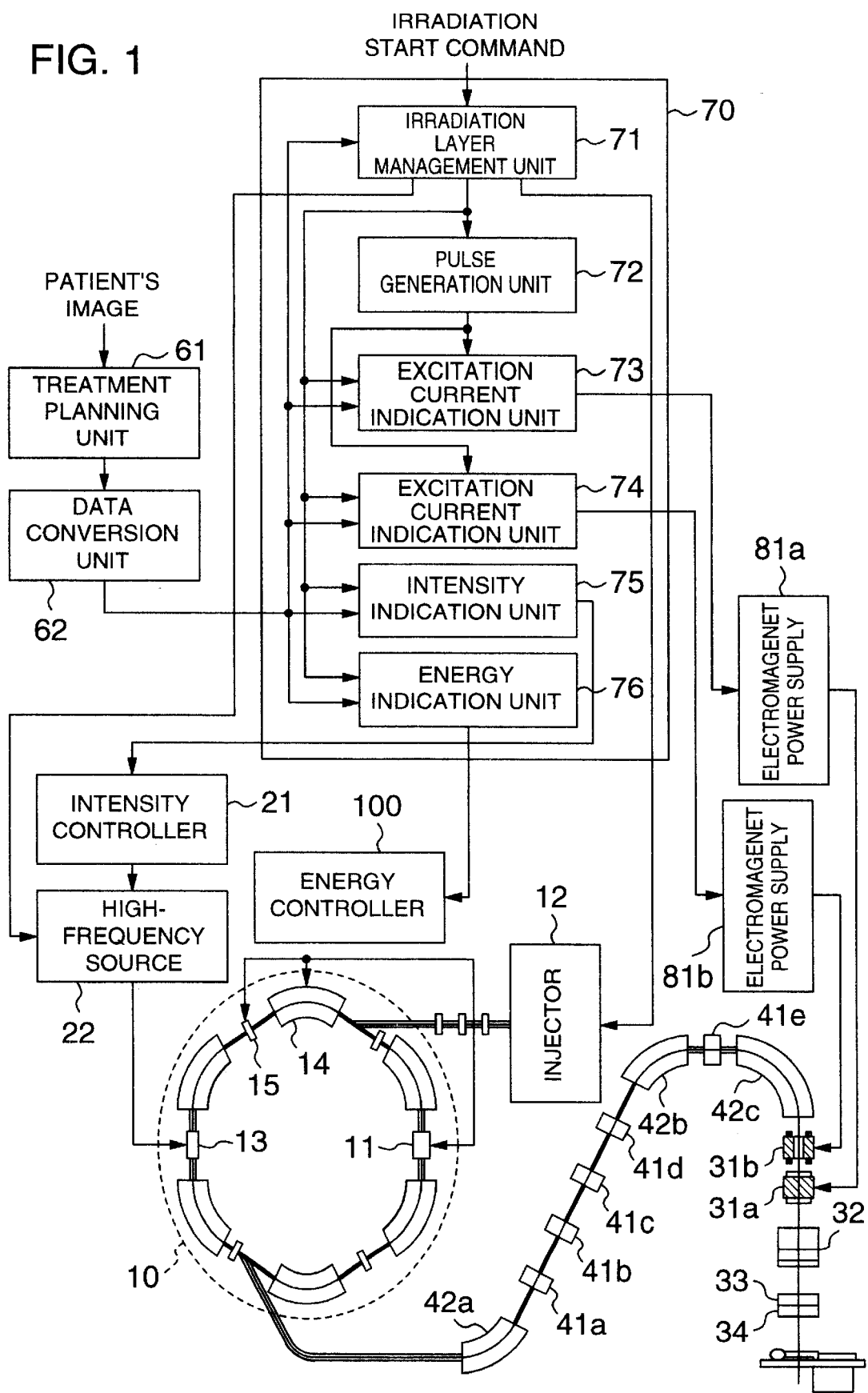
FIG. 1 is a diagram showing the construction of a charged-particle beam irradiation system according to a preferred embodiment of the present invention.

FIG. 1 shows a charged-particle beam irradiation system according to a preferred embodiment of the present invention. In FIG. 1, a treatment planning unit 61 determines the depth of an affected part of a patient in the body thereof and a three-dimensional shape of the affected part from an image of the affected part obtained by a CT apparatus (not shown) and determines the dose of a charged-particle beam (hereinafter referred to as a beam) and the range and direction of irradiation on the basis of the determined three-dimensional shape. On the basis of the depth of the affected part in the body, the dose of the beam and the range and direction of irradiation determined by the treatment planning unit 61, a data conversion unit 62 determines the number n of plural layers into which the affected part is to be divided in the irradiation direction of the beam, the energy and intensity of the beam which is to be imparted for each layer, and the patterns of excitation current values for scanning electromagnets 31a and 31b when each layer is to be irradiated. The determined data is outputted to a controller 70.

In the determined pattern, the current value data is defined so that the scanning speed of the beam is changed at a region which is subjected to superimposed irradiation. This holds for other embodiments.

In the present embodiment, the treatment planning unit 61 and the data conversion unit 62 are provided as separate units. However, the same unit may have the functions of both of the units 61 and 62. Also, the controller 70 may have the function of the data conversion unit 62.

The controller 70 includes an irradiation layer management unit 71 for managing the number n of layers to be irradiated and a layer number i of a layer being irradiated at present, a pulse generation unit 72 for outputting a pulse signal at a constant period, excitation current indication units 73 and 74 for indicating excitation current values to electromagnet power supplies 81a and 81b which supply excitation currents for the scanning electromagnets 31a and 31b, an intensity indication unit 75 for indicating the intensity of a beam for irradiation to an intensity controller 21 which controls the intensity of the beam for irradiation, and an energy indicating unit 76 for indicating the energy of the beam for irradiation to an energy controller 100 which controls the energy of beam for irradiation. In the controller 70, the number n of layers, the patterns of excitation current values for the scanning electromagnets 31a and 31b at the time of irradiation of each layer, the intensity of the beam for each layer and the energy of the beam for each layer inputted from the data conversion unit 62 are stored into the irradiation layer management unit 71, the excitation current indication units 73 and 74, the intensity indication unit 75 and the energy indication unit 76, respectively. In the present embodiment, a raster scanning method of scanning in zigzag rasters is used as a beam scanning method and the excitation current value patterns for the scanning electromagnets 31a and 31b are set so that the beam is zigzag-wise scanned.

In the controller 70, when an irradiation start command is inputted from an operator, the irradiation layer management unit 71 outputs "1" to the excitation current indication units 73 and 74, the intensity indication unit 75 and the energy indication unit 76 as the number i of a layer to be irradiated. The excitation current indication units 73 and 74 indicate excitation current values to the electromagnet power supplies 81a and 81b on the basis of the stored excitation current value patterns and the inputted layer number "1" so that an initial irradiation position in the first layer is to be subjected to irradiation with a beam. The intensity indication unit 75 indicates the intensity of a beam in the first layer to the intensity controller 21 on the basis of the stored beam intensity data for each layer and the inputted layer number "1". Also, the energy indication unit 76 indicates the energy of a beam corresponding to the first layer to the energy controller 100 on the basis of the stored beam energy data for each layer and the inputted layer number "1". In the present embodiment, the irradiation with the beam is made in a sequence from a deep layer (or a layer existing at the deepest position in the beam progressing direction) to a shallow layer (or the shallowest layer). Accordingly, the first layer indicates a layer which exists at the deepest position.

The electromagnet power supplies 81a and 81b excite the scanning electromagnets 31a and 31b on the basis of the indicated excitation current values. The scanning electromagnets 31a and 31b generate magnetic fields corresponding to the indicated excitation current values so that the irradiation position of a beam is set to an initial irradiation position in accordance with the generated magnetic fields.

On the basis of the indicated beam intensity, the intensity controller 21 determines the power value and frequency range of a high-frequency electric power to be outputted by an ejecting high-frequency source 22. In the intensity controller 21, a relationship between the beam intensity and the power value and frequency range of the high-frequency electric power is tabulated beforehand. The determined power value and frequency range are outputted to the ejecting high-frequency source 22. The ejecting high-frequency source 22 applies a high-frequency electric power having the inputted power value and frequency range to an ejecting high-frequency electrode 13 of a synchrotron 10 in accordance with an ejection command from the irradiation layer management unit 71. In the synchrotron 10 in the present embodiment, the oscillation amplitude of a beam being circulated is increased by applying a high-frequency electric field to the beam in a state in which the limit of stability of the beam is kept constant, and the beam exceeding the stability limit owing to the increase in oscillation amplitude is ejected by use of resonance. The ejecting high-frequency electrode 13 is provided for applying the high-frequency electric field which increases the oscillation amplitude. With this synchrotron 10, it is possible to control the intensity of a beam for irradiation by controlling the power value and frequency range of a high-frequency electric power to be applied to the ejecting high-frequency electrode 13 which applies the high-frequency electric field to the beam. The beam intensity may be controlled by controlling one of the power value and frequency range of the high-frequency electric power. The control of the power value may be performed by merely adjusting the gain of an amplifier and can therefore be performed simply as compared with the control of the frequency range.

The energy controller 100 controls a high-frequency accelerating cavity 11, a deflecting electromagnet 14 and a quadruple electromagnet 15 so that a beam circulating in the synchrotron 10 has the indicated energy.

Next, the irradiation layer management unit 71 instructs an injector 12 to inject a beam into the synchrotron. The instructed injector 12 injects the beam into the synchrotron. The beam injected into the synchrotron is accelerated by the high-frequency accelerating cavity 11, the deflecting electromagnet 14 and the quadruple electromagnet 15 up to the energy indicated by the energy indication unit 76.

After the completion of acceleration of the beam, the irradiation layer management unit 71 outputs an ejection command to the ejecting high-frequency source 22 and outputs a pulse generation start command to the pulse generation unit 72. The ejecting high-frequency source 22 inputted with the ejection command applies a high-frequency electric power to the ejecting high-frequency electrode 13 so that a high-frequency electric field is applied from the ejecting high-frequency electrode 13 to the circulating beam and the beam is ejected from the synchrotron 10. The ejected beam passes through a beam transport system including quadruple electromagnets 41a, 41b, 41c, 41d and 41e and deflecting electromagnets 42a, 42b and 42c and is then introduced to an irradiation device which includes scanning electromagnets 31a and 31b, a degrader 32, a beam position monitor 33 and a dose monitor 34. The beam is imparted to an initial irradiation position by virtue of magnetic fields generated by the scanning electromagnets 31a and 31b.

Figure 10:
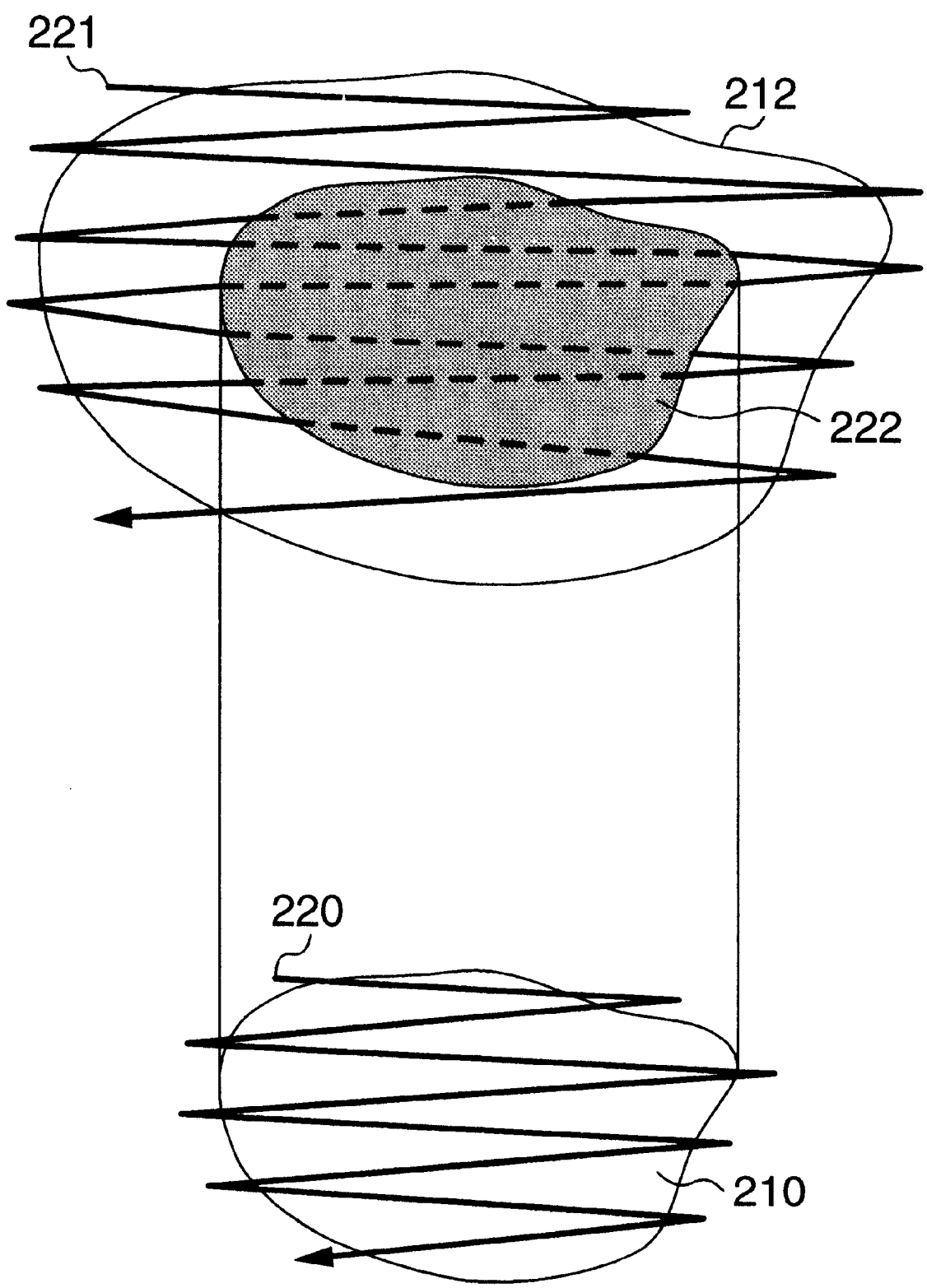
FIG. 10 is a diagram showing a charged-particle beam scanning method based on a raster scanning method.
Figure 11:
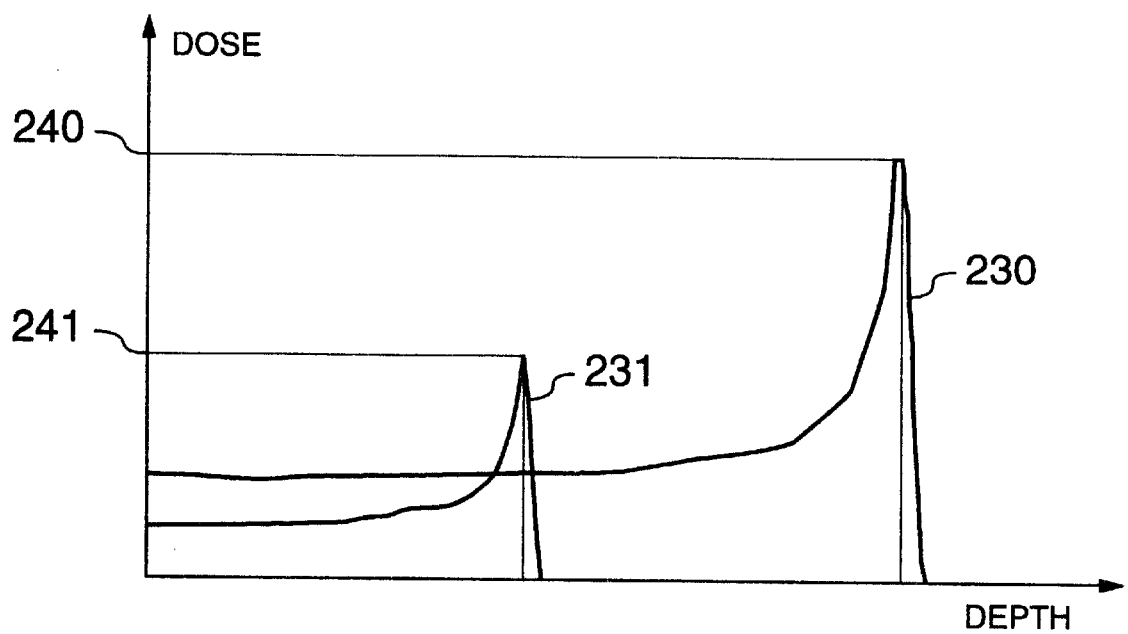
FIG. 11 is a graph showing the relation of a dose with the depth in a body.

After receiving the pulse generation start command, the pulse generation unit 72 outputs a pulse signal to the excitation current indication units 73 and 74 at a constant period. The excitation current indication units 73 and 74 inputted with the pulse signal change, on the basis of the excitation current value patterns stored therein, the excitation current values indicated to the electromagnet power supplies 81a and 81b so that the beam is imparted to the next irradiation position. The electromagnet power supplies 81a and 81b excite the scanning electromagnets 31a and 31b on the basis of the changed excitation current values. The scanning electromagnets 31a and 31b generate magnetic fields corresponding to the changed excitation current values so that the irradiation position of the beam is moved from the initial irradiation position to the next irradiation position. In this manner, each time the pulse signal is generated, the change of the excitation current values indicated to the electromagnet power supplies 81a and 81b is repeated so that the irradiation position is moved. Thereby, the first layer is irradiated with the beam which is zigzag-wise scanned, as shown in FIG. 10. In the case where the first layer is irradiated, the radiation dose of the beam may be constant. That is, the scanning speed of the beam may be constant. Therefore, the moving distance of the beam (or the amount of change in excitation current value) at the time of movement from a certain irradiation position to the next irradiation position may be constant.

At a time of point when the scanning for the first layer based on the excitation current value patterns is completed, the irradiation layer management unit 71 outputs a stop command to the pulse generation unit 72, the intensity indication unit 75 and the energy indication unit 76. Receiving the stop command, the pulse generation unit 72 stops the output of the pulse signal. The intensity indication unit 75 stops the indication of the beam intensity, thereby stopping the application of the high-frequency electric power to the ejecting high-frequency electrode 13 and the ejection of the beam. The energy indication unit 76 instructs the energy controller 100 to decelerate the beam to a predetermined speed. Thus, in the present embodiment, the irradiation with the beam is stopped after the irradiation of the first layer is completed.

Next, the irradiation layer management unit 71 outputs "2" to the excitation current indication units 73 and 74, the intensity indication unit 75 and the energy indication unit 76 as the number i of a layer to be irradiated.

The excitation current indication units 73 and 74 indicate excitation current values to the electromagnet power supplies 81a and 81b on the basis of the stored excitation current value patterns and the inputted layer number "2" so that an initial irradiation position in the second layer is subjected to irradiation with a beam. The second layer includes a region subjected to irradiation at the time of irradiation of the first layer. Therefore, it is necessary to increase a scanning speed in such a region as compared with that in a region which has not yet been irradiated. Accordingly, excitation current value patterns corresponding to the second layer are set so that a distance between irradiation positions (or the amount of change in excitation current value) becomes large in the region having already been irradiated. In the present embodiment, since the pulse signal is outputted from the pulse generation unit 72 at the constant period, the scanning speed can be increased by making the distance between irradiation positions long.

The intensity indication unit 75 indicates the intensity of a beam in the second layer to the intensity controller 21 on the basis of the stored beam intensity data for each layer and the inputted layer number "2". The beam intensity in the second layer is set to be low as compared with the beam intensity in the case of the first layer. As mentioned above, the second layer includes a region subjected to irradiation at the time of irradiation of the first layer. Therefore, if the second layer is irradiated at the same beam intensity as that for the first layer, it is necessary to increase the scanning speed for the second layer as compared with that for the first speed in order to reduce a radiation dose in the region having already been irradiated. In the present embodiment, on the other hand, it is possible to suppress the increase of the scanning speed by making the beam intensity low.

A method for determination of the beam intensity for the second layer in the present embodiment will be described in the following. Now, it is assumed that a dose to be imparted to the whole of the affected part is 10 and the beam intensity in the first layer is 1. In the case where a radiation dose in the region of the second layer having already been irradiated is 5, the beam intensity in the second layer is set to 0.5. By thus setting the beam intensity in the second layer, the beam scanning speed in the first layer and the beam scanning speed in the region of the second layer having already been irradiated become equal to each other. Namely, the beam scanning speed is the same in both the case where the dose of 10 is imparted at the beam intensity of 1 and the case where the dose of 5 is imparted at the beam intensity of 0.5. The scanning speed in a region of the second layer having not yet been irradiated becomes one half of the scanning speed in the first layer in order to impart the dose of 10 at the beam intensity of 0.5. Thus, the beam intensity in the second layer is set such that the maximum scanning speed in the second layer becomes equal to the scanning speed in the first layer. On the other hand, if the first layer and the second layer are irradiated at the same beam intensity, as in the prior art, it is required that the scanning speed in the region of the second layer having already been irradiated should be made two times as high as that in the first layer.

The energy indication unit 76 inputted with "2" as the layer number i indicates the energy of a beam corresponding to the second layer to the energy controller 100 on the basis of the stored beam energy data for each layer and the inputted layer number "2". Since the second layer exists at a position shallower than the first layer, the beam energy is set to a low value. Namely, a required energy becomes smaller as the position of a layer is shallower.

In a manner similar to that in the case of irradiation of the first layer, the beam is ejected from the synchrotron and the ejected beam is scanned to irradiate the second layer with the beam.

Similar irradiation is made for the third to n-th layers, thereby irradiating the whole of the affected part with the beam. As the layer position becomes shallower from the third layer to the n-th layer, a dose imparted beforehand (or having already been imparted) is increased and a dose distribution is complicated. In such a case, too, the beam intensity may be set so that the scanning speed in a region of the corresponding layer having already been irradiated with the largest dose takes a low value equal to the scanning speed in the first layer.

In the present embodiment as mentioned above, the beam intensity is set for each layer and it is therefore possible to lower the maximum value of the scanning speed as compared with the case where the beam intensity in each layer is made constant. The scanning speed is proportional to a change in magnetic field of the scanning electromagnets 31a and 31b with time, and this change in magnetic field with time is proportional to a change in current of the electromagnet power supplies 81a and 81b with time, that is, the output voltages of the electromagnet power supplies 81a and 81b. Therefore, when the maximum value of the beam scanning speed is reduced as in the present embodiment, the output voltages of the electromagnet power supplies 81a and 81b can be lowered and the cost of fabrication and operation of the electromagnet power supplies 81a and 81b can be reduced.

Also, the control of the beam intensity in the present embodiment based on the control of the power value and frequency range of the high-frequency electric power is an electric control. Therefore, a response is fast and a time required for changing the beam intensity is short. Accordingly, it is possible to shorten a treatment time.

In the present embodiment, the beam energy is changed in the synchrotron 10. However, the degrader 32 may be used for a fine control of the beam energy.

In the present embodiment, the beam intensity is set so that the scanning speed in a region of a layer having already been irradiated with the largest dose becomes equal to the scanning speed in the first layer. However, if the beam intensity is set with a mean dose value in a layer taken as a reference, a mean scanning speed value may be made equal to the scanning speed in the first layer, thereby making it possible to reduce the output voltages of the electromagnet power supplies 81a and 81b. Thus, the maximum value of the scanning speed can be lowered by reducing the beam intensity in the second to n-th layers even if there is any reduction.

(Embodiment 2)

Figure 2:
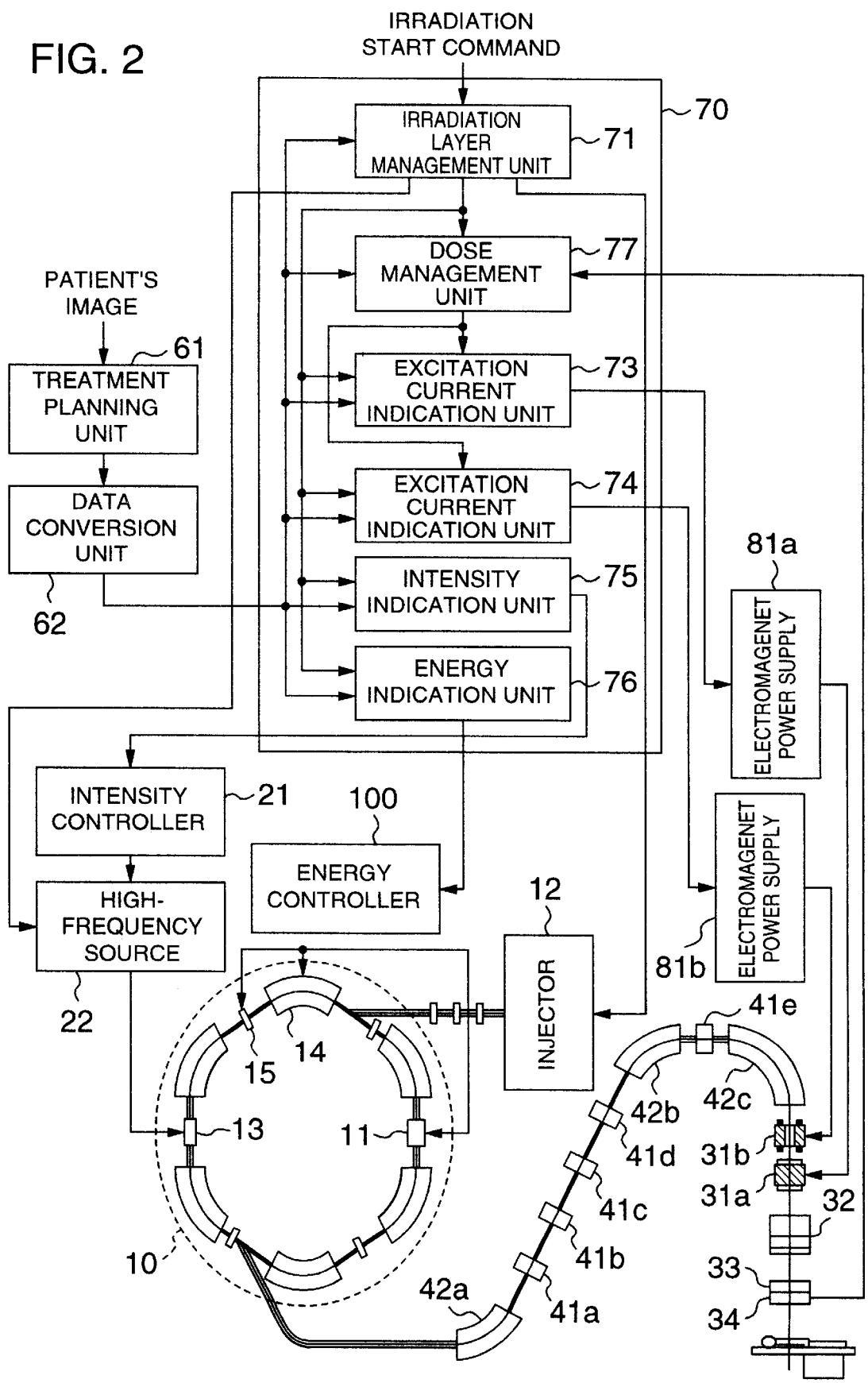
FIG. 2 is a diagram showing the construction of a charged-particle beam irradiation system according to another embodiment of the present invention.

A charged-particle beam irradiation system according to another embodiment of the present invention will now be described using FIG. 2. In the charged-particle beam irradiation system in the present embodiment, an instruction for change in irradiation position is made on the basis of a measured radiation dose. The present embodiment will be described in conjunction with points different from the first embodiment.

The irradiation system according to the present embodiment includes a dose management unit 77 provided in lieu of the pulse generation unit 72 in the first embodiment. In the present embodiment, the data conversion unit 62 determines the value of a radiation dose required at each irradiation position in a layer in addition to the number n of layers, the energy and intensity of a beam for each layer and the patterns of excitation current values for the scanning electromagnets 31a and 31b. This radiation dose value is outputted to the dose management unit 77. The dose management unit 77 stores therein the inputted radiation dose value in association with the corresponding irradiation position.

After the completion of beam acceleration, the irradiation management unit 71 outputs an ejection command to the ejecting high-frequency source 22 and outputs a dose management start command to the dose management unit 77. The dose management unit 77 inputted with the command from the irradiation layer management unit 71 compares a beam dose value measured by the dose monitor 34 with that one of the radiation dose values stored beforehand in association with irradiation positions which corresponds to an initial irradiation position. In the case where it is determined as the result of comparison that the measured beam dose value reaches the radiation dose value corresponding to the initial irradiation position, the dose management unit 77 outputs a pulse signal to the excitation current indication units 73 and 74. The excitation current indication units 73 and 74 inputted with the pulse signal changes excitation current values indicated to the electromagnet power supplies 81a and 81b on the basis of the stored excitation current value patterns so that an irradiation position is changed from the initial irradiation position to the next irradiation position.

Thereafter, the dose management unit 77 repeats the comparison of a beam dose value measured by the dose monitor 34 with that a radiation dose value stored beforehand in association with an irradiation position and outputs a pulse signal at a point of time when the measured beam dose value reaches the radiation dose value required at that irradiation position. With the irradiation position being thus changed each time the beam dose value reaches the required radiation dose value, the beam is scanned to irradiate each layer. In the present embodiment, the dose value from the dose monitor 34 may be taken in by taking in the dose value through an analog-to-digital converter or by generating a pulse in the case where there reaches a fixed dose and counting the number of pulses.

Points other than the above-described points are the same as those in the first embodiment.

According to the present embodiment, the following effect is provided in addition to the effects of the first embodiment. Namely, since a change in irradiation position is made in accordance with a dose value, it is possible to control a dose at each irradiation position accurately even if the intensity of a beam ejected from the synchrotron 10 has some variation.

In the present embodiment, when a layer is irradiated with a beam, the irradiation is continuously made without stopping the beam. However, there may be employed a method in which the irradiation with the beam is stopped in the case where a dose value measured by the dose monitor 34 and a dose value stored in the dose management unit 77 coincide with each other and the irradiation with the beam is made again after magnetic fields (or excitation currents) of the scanning electromagnets 31a and 31b are changed.

(Embodiment 3)

Figure 3:
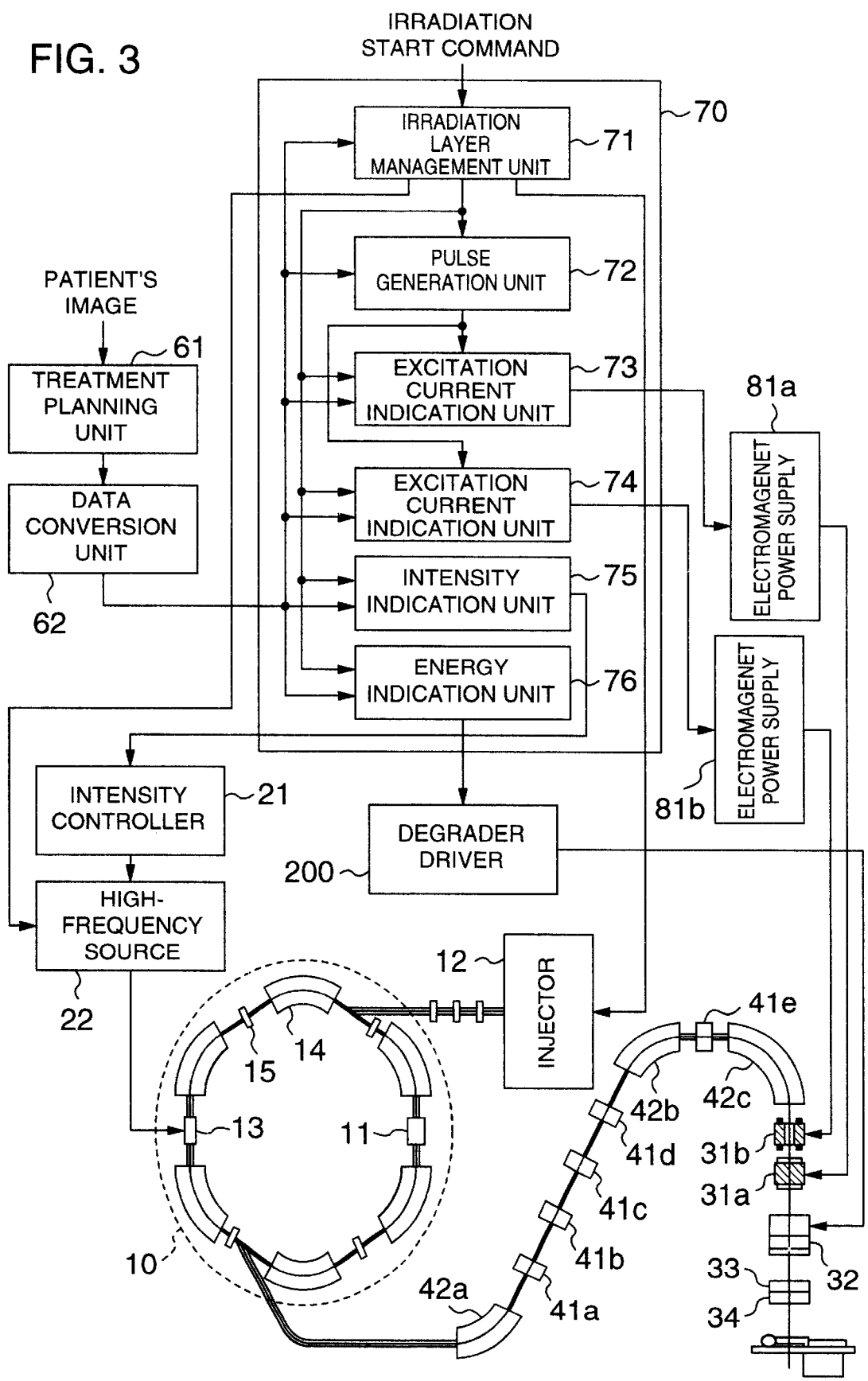
FIG. 3 is a diagram showing the construction of a charged-particle beam irradiation system according to still another embodiment of the present invention.

A charged-particle beam irradiation system according to still another embodiment of the present invention will now be described using FIG. 3. In the charged-particle beam irradiation system in the present embodiment, a change in beam energy is made by a degrader. The present embodiment will be described in conjunction with points different from the first embodiment.

The irradiation system according to the present embodiment includes a degrader driver 200 provided in lieu of the energy controller 100 in the first embodiment. In the present embodiment, the energy indication unit 76 indicates the energy of a beam to the degrader driver 200. The degrader driver 200 stores therein beforehand a relationship between the energy of a beam and a required degrader thickness and determines the thickness of the degrader 32 in accordance with the indicated energy. On the basis of the determined thickness, the degrader driver 200 further determines the combination of plates of the degrader 32 including a plurality of plates with different thicknesses so that the determined combination is arranged on the orbit. The plate forming the degrader 32 has a property of lowering the energy of a beam passing therethrough. In the present embodiment, the energy of a beam ejected from the synchrotron 10 is the maximum required energy and the degrader 32 is used in the case where there is a need to lower the energy.

Points other than the above-described points are the same as those in the first embodiment.

According to the present embodiment, the following effect is provided in addition to the effects of the first embodiment. Namely, since the beam energy is changed by the degrader 32, the control of the synchrotron can be simplified.

(Embodiment 4)

Figure 4:
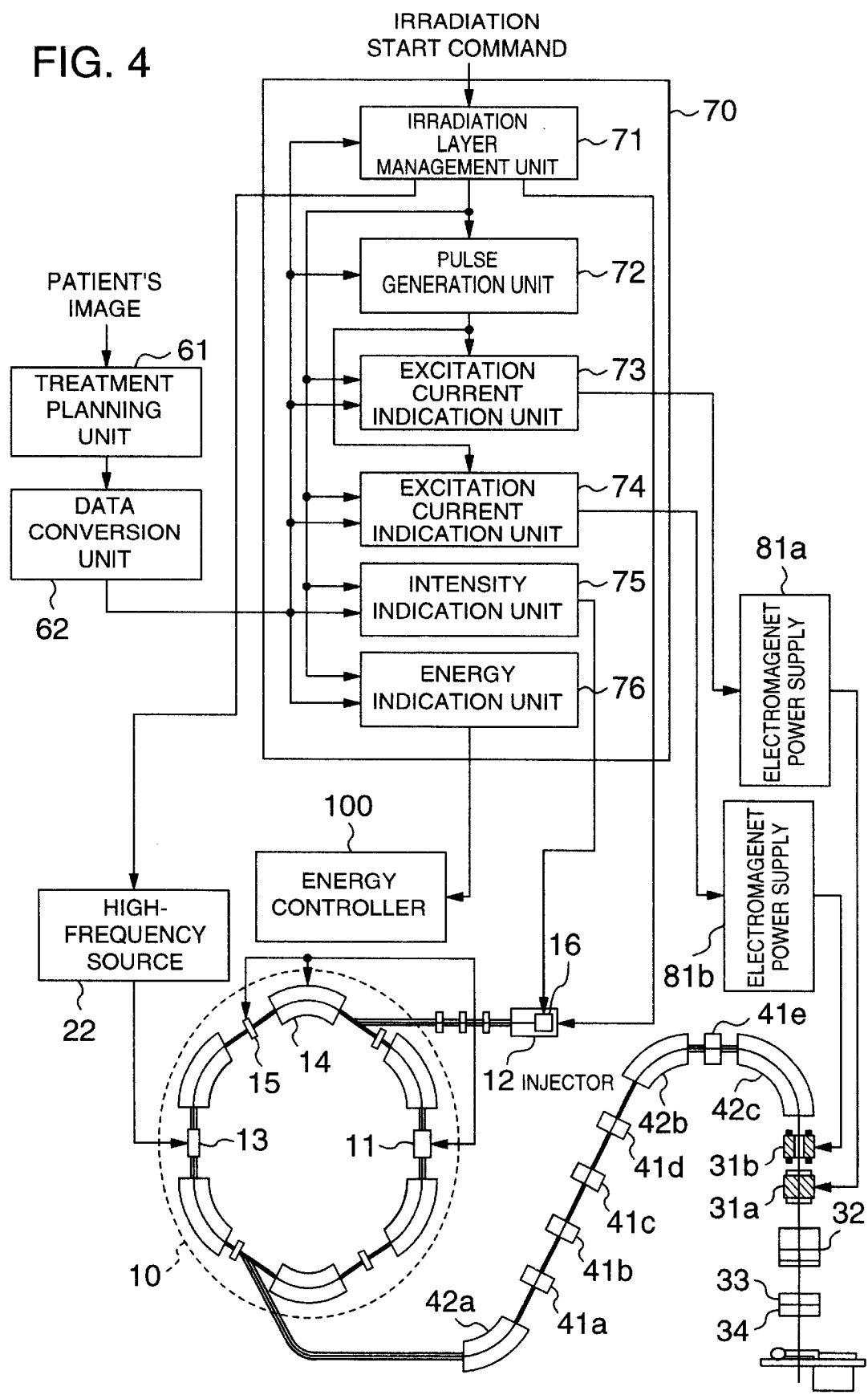
FIG. 4 is a diagram showing the construction of a charged-particle beam irradiation system according to a further embodiment of the present invention.

A charged-particle beam irradiation system according to a further embodiment of the present invention will now be described using FIG. 4. In the charged-particle beam irradiation system in the present embodiment, the intensity of a beam is changed by changing the amount of ions generated by an ion source 16 in the injector 12. The present embodiment will be described in conjunction with points different from the first embodiment.

The irradiation system according to the present embodiment has not the intensity controller 21. The intensity indication unit 75 indicates the intensity of a beam to the ion source 16. In accordance with the indicated beam intensity, the ion source 16 changes the amount of ions to be generated. Namely, as the indicated beam intensity is higher, the amount of generated ions becomes larger. In the present embodiment, a high-frequency electric power applied to the ejecting high-frequency electrode 13 is constant.

According to the present embodiment, the following effect is provided in addition to the effects of the first embodiment. Namely, since the amount of beams injected into the synchrotron 10 can be suppressed to the minimum required, it is possible to reduce unnecessary beams in the synchrotron 10, thereby reducing the (radio) activation of the equipment.

In the present embodiment, a slit may be provided in a beam transport system connecting the injector 12 and the synchrotron 10 so that the amount of ions injected into the synchrotron 10 is changed in accordance with the width of the slit.

In the foregoing, the embodiments has been described in conjunction with the case where a beam is zigzag-wise scanned. However, in each embodiment, a beam may be scanned pixel-wise. In this case, a control for ejecting the beam from the synchrotron 10 can be simplified. Now consider the case where the intensity of a beam in each layer is constant as in the prior art when the beam is pixel-wise scanned. In such a case, it is required that an irradiation time for a region of a shallower layer having already been irradiated should be made short. Therefore, the beam must be switched on and off at a short period, which complicates the control for beam ejection from the synchrotron 10. In the embodiment of the present invention, on the other hand, since the beam intensity in a shallower layer is made small, a beam irradiation time can be made long. Thereby, the control for beam ejection from the synchrotron 10 can be simplified, as mentioned above.

(Embodiment 5)

Figure 5:
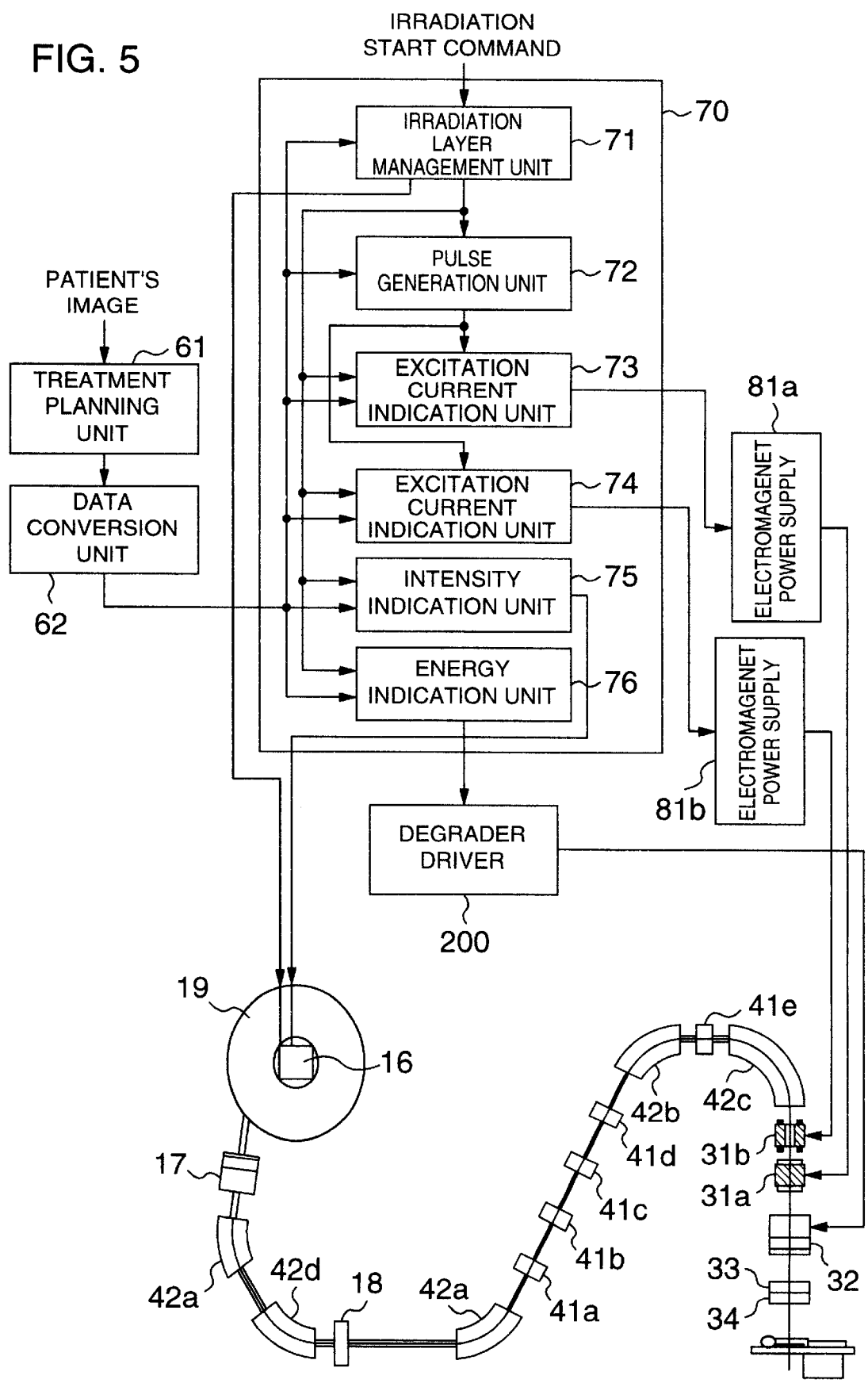
FIG. 5 is a diagram showing the construction of a charged-particle beam irradiation system according to still further embodiment of the present invention.

A charged-particle beam irradiation system according to a still further embodiment of the present invention will now be described using FIG. 5. In the charged-particle beam irradiation system in the present embodiment, a cyclotron is used as the accelerator. The present embodiment will be described in conjunction with points different from the third embodiment.

The intensity indication unit 75 indicates the intensity of a beam to an ion source 16' of a cyclotron 19 to control the amount of ions injected into the cyclotron 19 from the ion source 16' in accordance with the indicated beam intensity, thereby adjusting the intensity of a beam ejected from the cyclotron 19. In the present embodiment, an ejection command outputted from the irradiation layer management unit 71 is inputted to the ion source 16' of the cyclotron 19 and the ion source 16' injects a beam into the cyclotron 19 in accordance with this command. In the case where the ejection from the beam from the cyclotron 19 is stopped, a stop command is inputted from the irradiation layer management unit 71 to the ion source 16', thereby stopping the injection of the beam from the ion source 16' into the cyclotron 19.

In the present embodiment, the intensity of a beam is adjusted by controlling the amount of ions injected from the ion source into the cyclotron. However, a slit 18 may be provided in a beam transport system so that the beam intensity is adjusted in accordance with the width of the slit 18. Also, though the energy of a beam is controlled by the degrader 32, the control may be made by a degrader 17 provided in a downstream of the cyclotron 19. In the present embodiment, the accelerator may be a linear accelerator.

According to the present embodiment, effects similar to those in the third embodiment are obtained.

In the first to fourth embodiments, similar effects are obtained in the case where the intensity of a beam is changed by a slit provided in a beam transport system.

(Embodiment 6)

Figure 6:
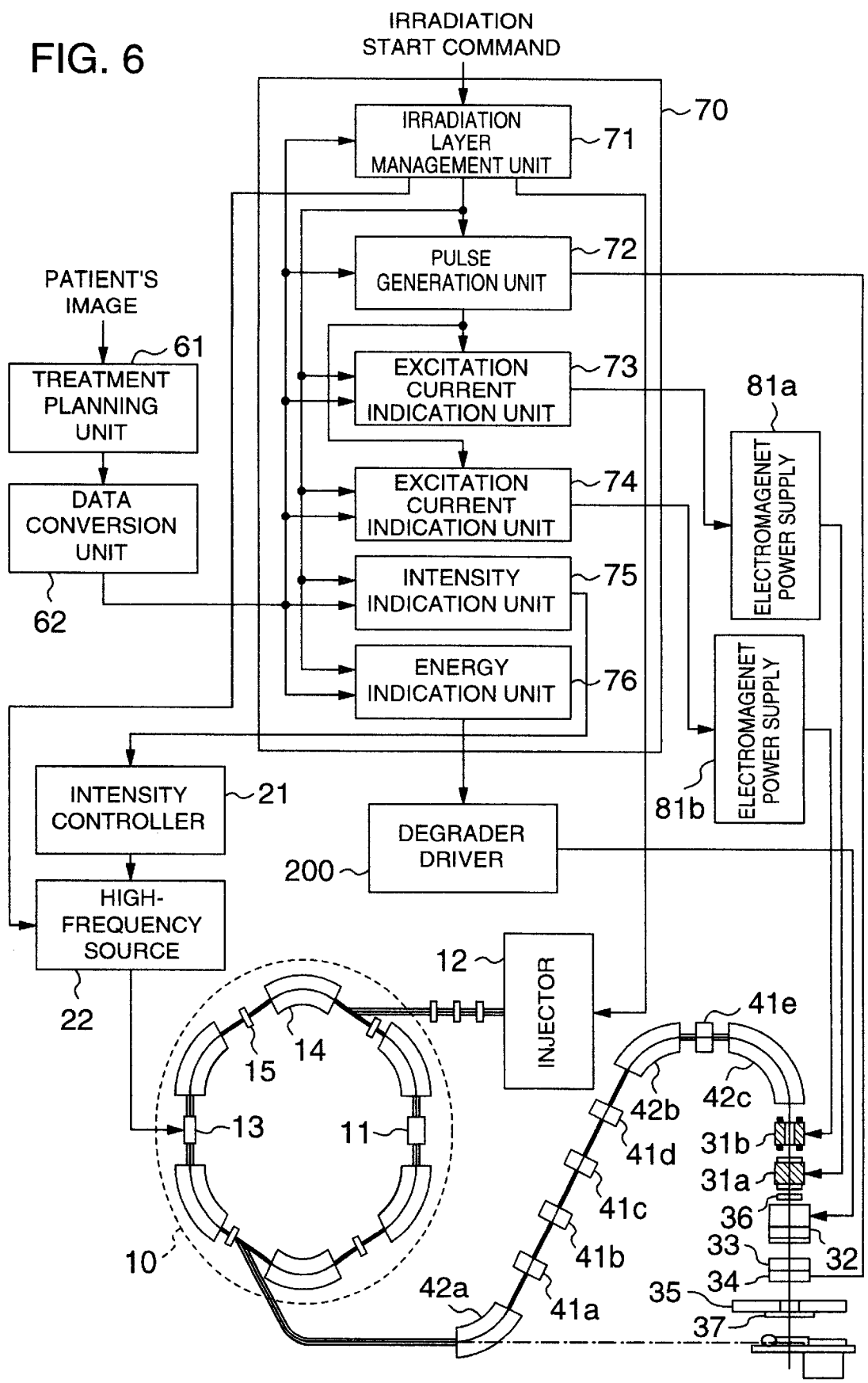
FIG. 6 is a diagram showing the construction of a charged-particle beam irradiation system according to a furthermore embodiment of the present invention.
Figure 7:
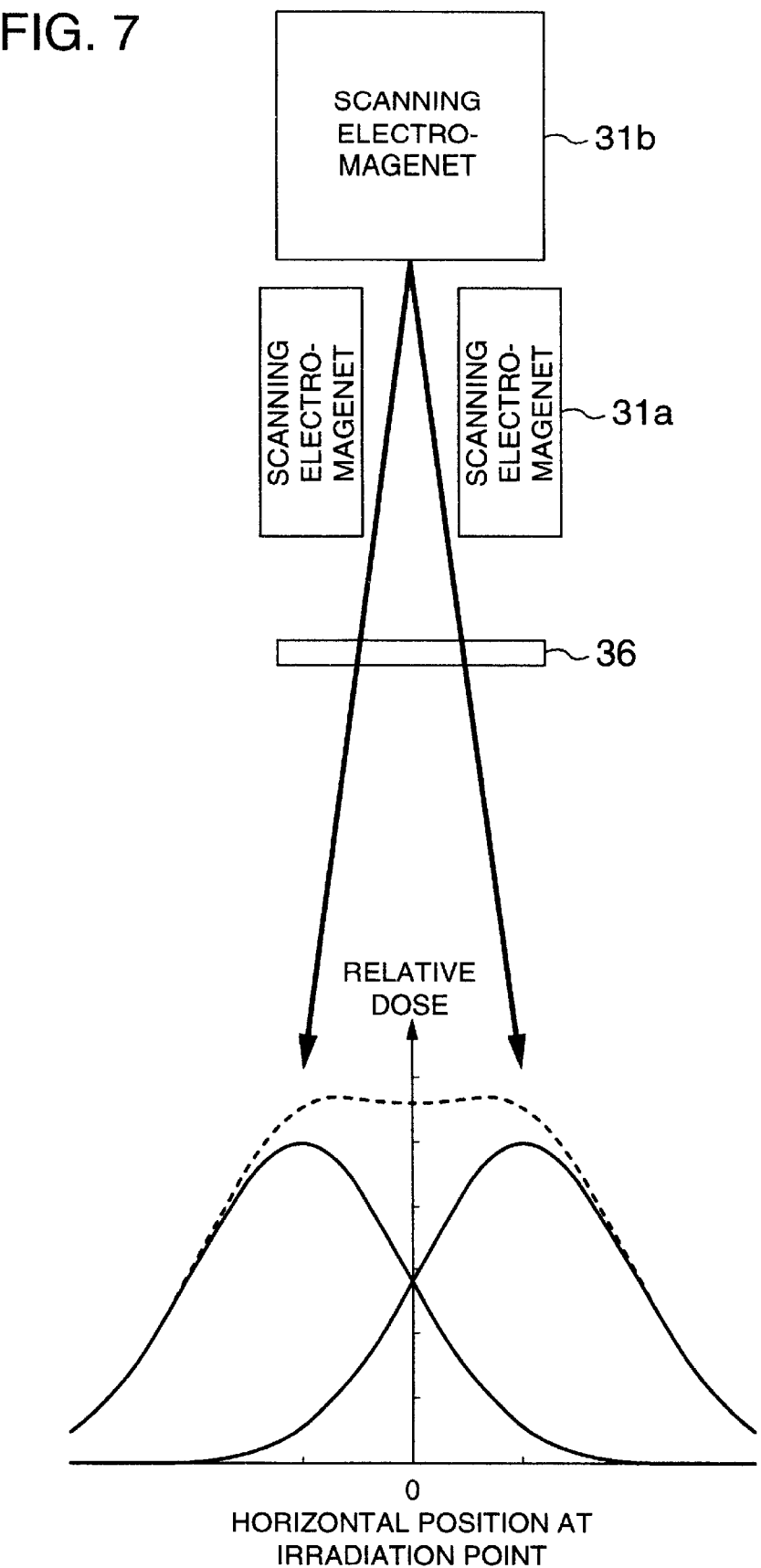
FIG. 7 is a diagram showing a detailed construction and a waveform for explaining the operation of the system shown in FIG. 6.
Figure 8:
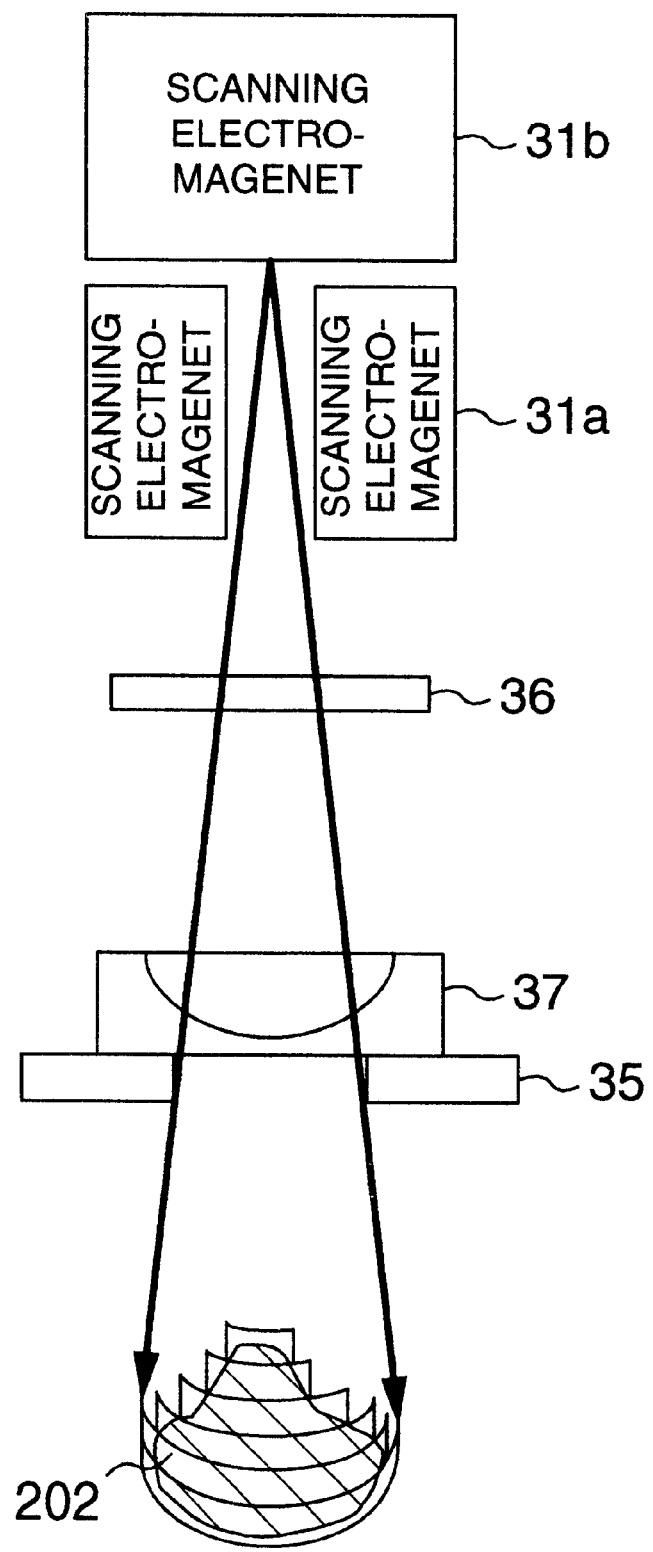
FIG. 8 is a diagram showing a detailed construction and the cross section of layers of an affected part for explaining the operation of the system shown in FIG. 6.
Figure 9:
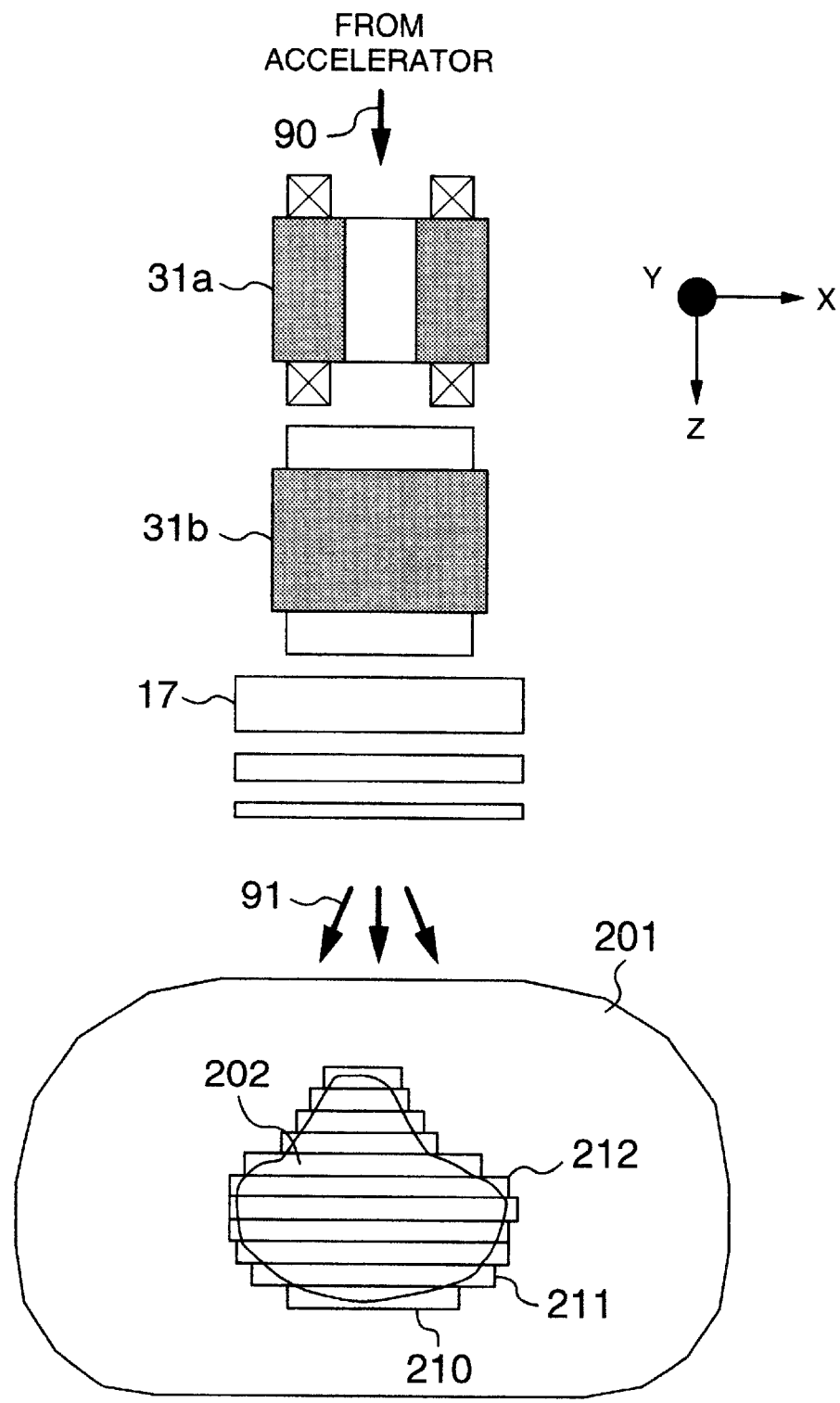
FIG. 9 is a view showing the construction of the conventional charged-particle beam irradiation system.

A charged-particle beam irradiation system according to a furthermore embodiment of the present invention will now be described using FIG. 6. FIGS. 7 and 8 are diagrams of the detailed construction showing the operation of the system. In the charged-particle beam irradiation system in the present embodiment, a beam is rotationally scanned circle-wise plural times as shown in FIG. 7 to produce a flat dose distribution and the dose distribution is imparted in a manner shaped by a multi-leaf collimator in conformity to the shape of an affected part as shown in FIG. 8. The present embodiment will be described in conjunction with points different from the third embodiment.

In the present embodiment, the patterns of excitation current values determined by the data conversion unit 62 are set so that a beam is circle-wise scanned at a constant speed. The patterns are stored in the excitation current indication units 73 and 74. Also, the data conversion unit 62 determines the radiation dose value of a beam required in each layer and stores it into the pulse generation unit 72. Further, the data conversion unit 62 outputs the intensity of a beam for each layer to the intensity indication unit 75. The beam intensity is set so that it becomes lower as that position of a layer is shallower.

When a pulse generation start command is inputted from the irradiation layer management unit 71, the pulse generation unit 72 generates a pulse signal to the excitation current indication units 73 and 74 at a constant period. The excitation current indication units 73 and 74 inputted with the pulse signal change excitation current values to be indicated to the electromagnet power supplies 81a and 81b on the basis of the stored excitation current value patterns each time the pulse signal is inputted. The scanning electromagnets 31a and 31b generate magnetic fields in accordance with excitation current values inputted from the electromagnet power supplies 81a and 81b so that a beam is scanned circle-wise at a constant speed. The circle-wise scanned beam is enlarged or spread by a scatterer 36 into a size larger than an affected part 202. A multi-leaf collimator 35 shapes the enlarged beam so that the beam conforms to the shape of the affected part. The range of the shaped beam is conformed by a bolus 37 to the shape of a lower portion of the affected part.

The dose monitor 34 measures the dose value of a beam to output the measured value to the pulse generation unit 72. The pulse generation unit 72 compares the stored radiation dose value for each layer and the measured dose value to stop the output of the pulse signal to the excitation current indication units 73 and 74 when the measured dose value reaches the stored radiation dose value. Thus, at a point of time when the irradiation of a layer is completed, the irradiation layer management unit 71 outputs a stop command to the intensity indication unit 75 and the energy indication unit 76.

Points other than the above-described points are the same those in third embodiment.

Consider the case where each layer is irradiated with a beam scanned circle-wise plural times, as in the present embodiment. In this case, if the intensity of a beam in a shallower layer is made equal to the intensity of a beam in a deeper layer, a beam irradiation time becomes short in the shallower layer in order to make a dose small and hence the number of beam rotations becomes small. At this time, if variations in the beam intensity with time are generated, the uniformity of a dose distribution is deteriorated. Also, the rise and fall of the beam resulting from the turn-on/off thereof give a larger influence on the dose distribution. In the present embodiment, however, the intensity of a beam is made lower as the position of a layer becomes shallower. Thereby, it is possible to make the irradiation time long. As a result, the uniformity of the dose distribution can be improved by making the number of rotational scans large.

The first to fourteenth inventions defined in the description of SUMMARY OF THE INVENTION and represented by the above-described embodiments provide the following effects.

According to the first and eighth inventions, since a voltage to be applied to the electromagnet can be lowered, it is possible to reduce the cost of a power supply for the electromagnet. Also, the control of the accelerator is simplified.

According to the second and ninth inventions, since a voltage to be applied to the electromagnet can be lowered, it is possible to reduce the cost of a power supply for the electromagnet. Also, the control of the accelerator is simplified.

According to the third and tenth inventions, it is possible to shorten a time required for the change in beam intensity, thereby shortening a treatment time.

According to the fourth and eleventh inventions, the control of a high-frequency electric field is simplified.

According to the fifth and twelfth inventions, it is possible to reduce unnecessary beams in the accelerator, thereby reducing the (radio) activation of the equipment.

According to the sixth and thirteenth inventions, it is possible to control a dose in each layer accurately even if the intensity of a charged-particle beam ejected from the accelerator has some variations.

According to the seventh and fourteenth inventions, the control of the accelerator is simplified.

What is claimed is:

1. A charged-particle beam irradiation method in which while a charged-particle beam ejected from an accelerator is scanned by an electromagnet, each layer resulting from the division of an affected part into a plurality of layers in the direction of progression of said charged-particle beam is irradiated with the charged-particle beam, wherein the intensity of a charged-particle beam for irradiation of a first layer is made lower than the intensity of a charged-particle beam for irradiation of a second layer existing at a position deeper than said first layer in the beam progressing direction, and a scanning speed in said first layer is changed between a portion of said first layer subjected to irradiation at the time of irradiation of said second layer and a portion of said first layer subjected to no irradiation at the time of irradiation of said second layer.

2. A charged-particle beam irradiation method in which while a charged-particle beam ejected from an accelerator is scanned by an electromagnet, each layer resulting from the division of an affected part into a plurality of layers in the direction of progression of said charged-particle beam is irradiated with the charged-particle beam, wherein the intensity of said charged-particle beam for irradiation of each layer is made lower as the position of that layer becomes shallower in the beam progressing direction, and a scanning speed in a shallower layer is changed between a portion of said shallower layer subjected to irradiation at a flat portion of a charged-particle beam characteristic at the time of irradiation of a deeper layer and a portion of said shallower layer subjected to no irradiation at the time of irradiation of said deeper layer.

3. A charged-particle beam irradiation method according to claim 1 or 2, wherein said accelerator includes a synchrotron for ejecting a charged-particle beam through the application of a high-frequency electric field thereto, and the intensity of said charged-particle beam is controlled by controlling said high-frequency electric field.

4. A charged-particle beam irradiation method according to claim 3, wherein said high-frequency electric field is generated from an electrode applied with a high-frequency electric power, and said high-frequency electric field is controlled by controlling the power value of said high-frequency electric power.

5. A charged-particle beam irradiation method according to claim 1 or 2, wherein the intensity of said charged-particle beam is controlled by controlling the amount of ions injected into said accelerator.

6. A charged-particle beam irradiation method according to claim 1 or 2, wherein the scanning of said charged-particle beam is performed on the basis of the dose value of said charged-particle beam.

7. A charged-particle beam irradiation method according to claim 1 or 2, wherein a layer to be irradiated with said charged-particle beam is changed by changing the energy of said charged-particle beam, and said change in energy is made by a degrader disposed on an orbit of said charged-particle beam.

8. A charged-particle beam irradiation system in which while a charged-particle beam ejected from an accelerator is scanned by an electromagnet, each layer resulting from the division of an affected part into a plurality of layers in the direction of progression of said charged-particle beam is irradiated with the charged-particle beam, the system comprising:

intensity control means for making the intensity of a charged-particle beam for irradiation of a first layer lower than the intensity of a charged-particle beam for irradiation of a second layer existing at a position deeper than said first layer in the beam progressing direction; and scanning speed changing means for changing a scanning speed in said first layer between a portion of said first layer subjected at the time of irradiation of said second layer and a portion of said first layer subjected to no irradiation at the time of irradiation of said second layer.

9. A charged-particle beam irradiation system in which while a charged-particle beam ejected from an accelerator is scanned by an electromagnet, each layer resulting from the division of an affected part into a plurality of layers in the direction of progression of said charged-particle beam is irradiated with the charged-particle beam, the system comprising:

intensity control means for making the intensity of said charged-particle beam for irradiation of each layer lower as the position of that layer becomes shallower in the beam progressing direction; and scanning speed changing means for changing a scanning speed in a shallower layer between a portion of said shallower layer subjected to irradiation at a flat portion of a charged-particle beam characteristic at the time of irradiation of a deeper layer and a portion of said shallower layer subjected to no irradiation at the time of irradiation of said deeper layer.

10. A charged-particle beam irradiation system according to claim 8 or 9, wherein said accelerator includes a synchrotron for ejecting a charged-particle beam through the application of a high-frequency electric field thereto, and there is provided control means for controlling said high-frequency electric field to control the intensity of said charged-particle beam.

11. A charged-particle beam irradiation system according to claim 10, wherein said high-frequency electric field is generated from an electrode applied with a high-frequency electric power, and there is provided control means for controlling the power value of said high-frequency electric power to control said high-frequency electric field.

12. A charged-particle beam irradiation system according to claim 8 or 9, wherein there is provided control means for controlling the amount of ions injected into said accelerator to control the intensity of said charged-particle beam.

13. A charged-particle beam irradiation system according to claim 8 or 9, wherein there is provided control means for performing the scanning of said charged-particle beam on the basis of the dose value of said charged-particle beam.

14. A charged-particle beam irradiation system according to claim 8 or 9, wherein a layer to be irradiated with said charged-particle beam is changed by changing the energy of said charged-particle beam, and there is provided a degrader disposed on an orbit of said charged-particle beam for making said change in energy.

* * * * *